United States Patent
Pauson et al.

(10) Patent No.: US 6,174,840 B1
(45) Date of Patent: *Jan. 16, 2001

(54) USE OF FUSED RING CYCLOPENTANONES AND CYCLOPENTENONES IN CONTROLLING PLANT GROWTH

(75) Inventors: Peter Ludwig Pauson, Glasgow; Ralph Christie Kirkwood, Ayr, both of (GB); Milan Hudecek, Bratislava (SK)

(73) Assignee: The University of Strathclyde, Glasgow (GB)

( * ) Notice: Under 35 U.S.C. 154(b), the term of this patent shall be extended for 0 days.

This patent is subject to a terminal disclaimer.

(21) Appl. No.: 09/269,912

(22) PCT Filed: Nov. 23, 1993

(86) PCT No.: PCT/GB93/02405

§ 371 Date: Oct. 24, 1995

§ 102(e) Date: Oct. 24, 1995

(87) PCT Pub. No.: WO94/12029

PCT Pub. Date: Jun. 9, 1994

(30) Foreign Application Priority Data

Nov. 23, 1992 (GB) .................................. 9224517

(51) Int. Cl.$^7$ ............................. A01N 35/06; A01N 43/12
(52) U.S. Cl. ............................. 504/298; 504/313; 504/348
(58) Field of Search .................................. 504/298, 313, 504/348

(56) References Cited

U.S. PATENT DOCUMENTS 4,143,230   3/1979   Greene et al. ........................ 562/504

FOREIGN PATENT DOCUMENTS

1052951   * 12/1966   (GB) .

OTHER PUBLICATIONS

I. Popova et al., "Antiperspirant property of jasminic acid.", Chemical Abstracts 109, 187574x (1988).
D. Gross, "Plant Growth Regulatory Substances Both of Microbial and Plant Origin", Chemistry of Plant Protection, Ed. W. Ebbing, Springer–Verlag, Berlin, (1991), vol. 7, pp. 6–11 & 42–45.
I. Khand et al., "Organocobalt Complexes. Part XI. A General Synthetic Route to Cyclopentenones . . .", J. Chem. Research (S), 9 (1977).
D.C. Billington et al., "Synthesis of Jasmone, Jasmonic Acid and Some Analogues . . .", J. Chem. Research (S), 2601–2622 (1988).
D.C. Billington et al., "The effect of ultrasound and of phosphine and phosphine oxides on the Khand reaction", J. Organometallic Chem. 354, 233–242 (1988).
Y. Kamuro et al., "Preparation of epihydrojasmonates as plant growth regulators", Chemical Abstracts 117, 145341f (1992).
S. Shambayati et al., "N–oxide promoted Pauson–Khand Cyclizations at Room Temperature", Tetrahedron Letters 31, 5289–5292 (1990).
K.V. Thimann et al., "Relation between leaf senescence and Stomatal Closure . . . ", Proc. Natl. Acad. Sci. USA 76, 2295–2298 (1979).
E. Farmer et al., "Interplant Communication: Airborne methyl jasmonate . . . ", Proc. Natl. Acad. Sci. USA 87, 7713–7716 (1990).
U. Ravid et al., "Structures related to Jasmonic Acid and their effect on Lettuce Seedling Growth", J. Agric Food Chem. 23, 835–838 (1975).
B. Parthier, "Jasmonates: Hormonal Regulators or Stress Factors in Leaf Senescence?", J. Plant Growth Reg. 9, 57–63 (1990).
R.M. Tetley et al. "The Metabolism of Oat Leaves during Senescence", Plant Physiol. 54, 294–303 (1974).
S.O. Satler et al., "Le jasmonate de méthyle: nouveau et puissant", Comptes Rendus Acad Sc. Paris, 293, Série. III, 735–740 (1981).
I. Khand et al., "Organocobalt Complexes Part XI. A general synthetic route to cyclopentenones . . . ", J. Chem. Research (M), 168–187 (1977).
D. C. Billington et al., "Synthesis of Jasmone, Jasmonic Acid and Some Analogues . . . ", J. Chem. Research (M), 2601–2622 (1988).

* cited by examiner

Primary Examiner—S. Mark Clardy
(74) Attorney, Agent, or Firm—Nixon & Vanderhye

(57) ABSTRACT

Use in inhibiting plant growth of a compound of formula II

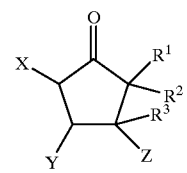

(II)

in which either the pair of symbols X and Y or the pair of symbols Y and Z, together with the carbon atoms to which they are attached, form a non-aromatic ring system having either 5 or 7 ring atoms, all of which are carbon except that one may be oxygen, and which is substituted or unsubstituted, $R^1$ represents a hydrogen atom or an alkyl, alkenyl or a substituted or unsubstituted phenyl group and $R^2$ represents a hydrogen atom and $R^3$ an alkyl carboxyalkyl group or $R^2$ and $R^3$ together form a double bond, and thereafter any unsatisfied valencies of ring carbon atoms of the ring shown in formula II are satisfied by hydrogen atoms.

11 Claims, No Drawings

USE OF FUSED RING CYCLOPENTANONES AND CYCLOPENTENONES IN CONTROLLING PLANT GROWTH

This application has been filed under 35 USC 371 as the national stage of international application PCT/GB 93/02405, filed Nov. 23, 1993.

BACKGROUND OF THE INVENTION

1. Field of the Invention

This invention relates to the control of plant growth and is particularly concerned with the use of certain fused cyclopentanones and cyclopentenones in the control of transpiration.

2. Description of the Related Art

There are many circumstances in which the use of plant growth retarding substances can be of considerable practical and economic significance, for example in control of the time of fruit ripening, bud sprouting or seed germination and in control of the extent of stem elongation (e.g. coleoptile growth). A further possible control is of transpiration via the stomatal apertures, thus giving control over the water balance of the plant. Control of the stomata, especially if reversible, can, for example, assist in the adaptation of crops to drought conditions and/or problems of salinity and alkalisation which may result from water shortage.

It has been known for some time that jasmonic acid and its simple carboxylic acid esters, eg methyl jasmonate, are involved in growth control. Thus Thimann et al (1979), Proc. Nat. Acad. Sci. USA, 716, 2295–2298 suggested that since methyl jasmonate is a volatile compound, it could be a volatile hormone involved in regulating the senescence and stomatal aperture of oat leaf segments. The formula (I) of methyl jasmonate is given below.

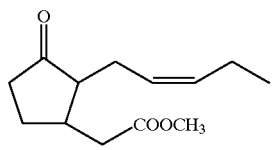

(I)

More recently, a review article by Parthier, J. Plant Growth Regulation (1990), 9, 57–63, in discussing the known stimulatory and inhibitory effects of jasmonic acid and methyl jasmonate, recounts the view that three important structural moieties are necessary for seedling growth inhibition (and probably for any biological activity): the acetoxy side chain, the n-pentenyl chain inserted at C-7, and a keto or hydroxy group at C-6.

It is against this background that a group of fused ring cyclopentanones and cyclopentenones have been found, which do not require all the structural features of methyl jasmonate or jasmonic acid and which surprisingly find application in the inhibition of transpiration.

SUMMARY OF THE INVENTION

Accordingly, the present invention provides the use in inhibiting plant growth, especially in controlling transpiration, of a compound of formula II

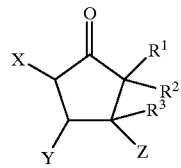

(II)

in which either the pair of symbols X and Y or the pair of symbols Y and Z, together with the carbon atoms to which they are attached, form a non-aromatic ring system having either 5 or 7 ring atoms, all of which are carbon except that one may be oxygen, and which is substituted or unsubstituted, $R^1$ represents a hydrogen atom or an alkyl or a substituted or unsubstituted phenyl group and $R^2$ represents a hydrogen atom and $R^3$ an alkyl carboxymethyl group or $R^2$ and $R^3$ together form a double bond, and thereafter any unsatisfied valencies of ring carbon atoms of the cyclopentanone or cyclopentenone ring shown in formula II are satisfied by hydrogen atoms.

DESCRIPTION OF THE PREFERRED EMBODIMENTS

X and Y or Y and Z preferably complete a cyclopentane, cycloheptane, [2.2.0] bicyclohexene or a tetrahydrofuran ring, substituted or unsubstituted.

$R^1$ is preferably an alkyl group of 1 to 6 carbon atoms, especially of 1 to 5 carbon atoms and preferably straight-chained or a phenyl, p-alkoxyphenyl or p-alkylcarbonylphenyl group in which the alkoxy and alkyl groups have 1 to 4 carbon atoms. p-Methoxyphenyl and p-Methylcarbonylphenyl (=p-acetylphenyl) are the preferred p-substituted phenyls.

When Y and Z represent a fused ring as defined above and simultaneously $R^2$ and $R^3$ represent a double bond, X is hydrogen in order to satisfy the unsatisfied valency in the ring of formula (II). When X and Y represent a fused ring as defined above and simultaneously $R^2$ is hydrogen and $R^3$ is alkyl carboxyalkyl, Z is hydrogen in order to satisfy the unsatisfied valency.

One preferred group of compounds for use in the composition of the invention is that in which X and Y or Y and Z together with the carbon atoms to which they are attached form a tetrahydrofuran ring, especially a tetrahydrofuran (THF) ring fused at the 3 and 4 positions to the cyclopentanone or cyclopentenone ring. Examples of such compounds are fused THF-cyclopentenones where $R^1$ is alkyl, especially of 1 to 6 carbon atoms, most especially of 1 to 5 carbon atoms, and/or where the THF ring is substituted at the 2-position, e.g. by dimethyl. Other examples are fused THF-cyclopentanones in which $R^2$ is hydrogen and RW is alkyl carboxymethyl. Preferably the alkyl groups of RW have from 1 to 4 carbon atoms.

Another preferred group of compounds for use in the invention are those of formula II in which X and Y together represent —$CH_2$—$(CH_2)_n$—$CH_2$— where n is 1 or 3, thus completing a cyclopentan or cycloheptane ring and $R^1$ represent an alkyl group of 1 or 3, thus 6 carbon atoms or a phenyl, p-alkoxyphenyl or p-alkylcarbonylphenyl in which the alkoxy and alkyl groups have 1 to 4 carbon atoms.

Where X and Y together represent a [2.2.0]bicyclohexene ring system, the double bond is preferably symmetrically disposed, i.e. it is a [2.2.0]bicyclohex-l-ene fused at the carbon atoms 4 and 5 as shown in Example 16.

Substituents $R^2$ and $R^3$ are preferably in the trans-configuration.

It will be appreciated that the compounds of formula II can exist in different stereoisomeric forms, the use of each of which is intended to be included within the present invention.

The preparation of the cyclopentanones and cyclopentenones of formula II can be conveniently effected employing the Khand reaction as described by Billington et al., (1988) J. Chem. Research (S) 326–327, (M) 2601–2622.

The Khand reaction requires co-cyclisation of alkynes with alkenes and carbon monoxide via an alkyne-octacarbonyldicobalt complex to give a cyclopentenone. The methods described by Billington et al may be employed to prepare various bicyclic and tricyclic compounds of formula II. In order to improve yields and extend the usefulness of the reaction the method may be accelerated by the use of amine oxides as described by Jeong et al, (1991), Synlett, 204 and Shambayati et al (1990), *Tetrahedron Letters*, 31, 5289.

Thus compounds where Y and Z together form a bicyclic or tricyclic ring structure are generally described by Jeong et al. Compounds where X and Y together form the ring structure are generally described by Billington et al.

The compounds of formula II have been found to demonstrate an effect on transpiration of plants by inducing stomatal closure.

The induction of stomatal closure is a prerequisite of antitranspirant activity. In plants, loss of water from leaf surfaces (transpiration) occurs through the stomatal pores (ca 95%); losses from the cuticle surfaces are minimal (ca 5%). The size of the stomatal pore is determined by the size and turgor of the guard cells which surround the pore; normally the pores exhibit a diurnal fluctuation, being open during daylight and closed at night. Loss of water is compensated by absorption of water by the roots and its movement via the xylem to the leaves. Inadequate water absorption due to drought or salinity may cause water stress and at least loss of crop productivity. Increasing frequency of drought and salinity on a world scale underlines the potential importance of a suitable antitranspirant.

The compounds were further found to exert an effect on other factors affecting growth, in particular shoot growth, as exemplified by indole-3-acetic acid (IAA) induced coleoptile growth.

The active compounds of formula II can be utilised, if desired, in the form of the usual formulations or compositions with one or more conventional inert (i.e. plant compatible or herbicidally inert) agricultural or horticultural carriers, e.g. conventional dispersible carrier vehicles such as gases, solutions, emulsions, wettable powders, suspensions, powders. dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations. The term "carrier" herein includes liquid carriers, often referred to as "diluents" or "diluent carriers".

These compositions can be prepared in known manner, for instance by extending the active compounds with conventional pesticide dispersible liquid diluent carriers and/or dispersible solid carriers optionally with the use of carrier vehicle assistants, e.g. conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as hydrocarbons, e.g. butane or propane, nitrogen or carbon dioxide; inert dispersible liquid diluent carriers, including inert organic solvents, such as aromatic hydrocarbons (e.g. benzene, toluene, xylene, alkyl naphthalenes), alcohols (e.g. methanol, ethanol, propanol, butanol, glycol) as well as ethers and esters thereof (e.g. ethylene glycol monomethyl ether), amines (e.g. ethanolamine), amides (e.g. dimethylformamide), sulfoxides (e.g. dimethylsulfoxide), acetonitrile, ketones (e.g. acetone, methyl ethyl ketone, methyl isobutyl ketone, cyclohexanone), and/or water; as solid carriers, ground natural minerals, such as clays especially kaolinite, talc, chalk, quartz, attapulgite, montmorillonite or diatomaceous earth, and ground synthetic minerals, such as highly-dispersed silicic acid, alumina and silicates; as solid carriers for granules including so-called volatile granules crushed and fractionated natural rocks such as calcite, marble, pumice, sepiolite or dolomite, as well as synthetic granules of inorganic and organic meals, and granules of organic material such as sawdust, coconut shells, maize cobs or tobacco stalks. The following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates or, especially, alkyl arylpolyglycol ethers, magnesium stearate or sodium oleate); and/or dispersing agents, such as lignin, sulfite waste liquors or methyl cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganse, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as insecticides, acaricides, nematicides, fungicides, bactericides, rodenticides, herbicides, and fertilisers, if desired, or in the form of particular dosage preparations for specific application made therefrom, such as solutions, emulsions, suspensions, powders, pastes, and granules which are thus ready for use.

As concerns commercially marketed preparations, these generally contemplate carrier compositions in which the active compound is present in an amount between 0.1–95% by weight, and preferably 0.5–90% by weight, of the mixture. Compositions suitable for direct application or field application generally contemplate those in which the active compound is present in an amount between 0.0001 to 1% (g./cm.$^3$), preferably 0.0001 to 0.4%. (g./cm.$^3$) and most preferably from $1\times10^{-5}$ molar to $1\times10^{-2}$ molar. Thus, the present invention contemplates overall compositions which comprise, especially a non-ionic surfactant, a conventional dispersible carrier such as (1) a dispersible inert finely divided carrier solid, and/or (2) a carrier liquid such as an inert organic solvent and/or water, said composition preferably including (3) a surface-active effective amount of a carrier vehicle assistant, e.g. a surface active agent, in addition to the active compound, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low volume process with good success, i.e. by applying such compound if normally a liquid, or by applying a liquid composition containing the same, via very effective atomising equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g hectare, preferably 40 to 600 g/hectare, are sufficient. In this process it is possible to use highly concentrated liquid compositions with said liquid carrier vehicles containing from about 20 to about 95% by weight of the active compound.

The invention further includes a method of controlling transpiration comprising applying to plants an effective amount of a composition comprising as active ingredient at least one compound of formula II as defined above.

The invention also includes a method of controlling shoot growth comprising applying to plants an effective amount of a composition comprising as active ingredient at least one compound of formula II as defined above.

The invention will now be illustrated by Examples. The compounds of the invention referred to therein are as follows:

| | Ring completed by | | | $R^2 + R^3$ or | |
| --- | --- | --- | --- | --- | --- |
| Ex. | X + Y | Y + Z | $R^1$ | $R^2$ | $R^3$ |
| 1 | THF | — | Pentyl | Double | bond |
| 2 | Cyclopentane | — | p-Methoxy-phenyl | " | " |
| 3 | Cycloheptane | — | Phenyl | " | " |
| 4 | — | THF | Pentyl | " | " |
| 5 | Cyclopentane | — | p-Acetyl-phenyl | " | " |
| 6 | — | THF | Pentyl | H | Methyl carboxy-methyl |
| 7 | Cyclopentane | — | p-Methoxy-phenyl | H | " |
| 8 | Cycloheptane | — | Phenyl | H | " |
| 9 | " | — | Pentyl | H | " |
| 10 | THF | — | Phenyl | H | " |
| 11 | Cyclopentane | — | Phenyl | Double | bond |
| 12 | — | 2,2-Dimethyl-THF | H | Double | bond |
| 13 | — | THF | Methyl | Double | bond |
| 14 | THF | — | Phenyl | Double | bond |
| 15 | Cyclopentane | — | Pentyl | Double | bond |
| 16 | [2.2.0] Bicyclo-hexene | — | Pentyl | Double | bond |
| 17 | Cyclopentane | — | Phenyl | H | Methyl carboxy-methyl |
| 18 | Cyclopentane | — | Pentyl | " | " |
| 19 | THF | — | Pentyl | " | " |

PREPARATIVE EXAMPLES

Yields relate to isolated products which were pure as judged by thin layer chromatography and absence of significant impurity peaks in nmr spectra.

EXAMPLE 1

1,3,3a, 6a-Tetrahydro-5-pentyl-4H-cyclopentan[c]furan-4-one

A 100 ml flask with magnetic stirrer and dropping funnel was charged with octacarbonyldicobalt (1.00 g, 0.924 mmol) and toluene (25 ml) and cooled in ice. 1-Heptyne (0.40 ml, 0.29 g, 3.0 mmol) in toluene (15 ml) was added over 10 min and stirring continued for a further 20 min at room temperature. 2,5-Dihydrofuran (2.2 ml, 2.05 g, 29 mmol) was added in one portion. Then a solution of trimethylamine-N-oxide dehydrate (2.93 g, 26.3 mmol) in methanol (6 ml) was added at a rate of 1 drop per min and stirring continued for a total of 24 h. Trimethylamine and methanol were then removed under vacuum, 2M hydrochloric acid (30 ml) was added and the mixture stirred until all precipitate had dissolved; then the layers were separated. The aqueous layer was extracted with ether (4×10 ml) and the combined organic layers dried ($MgSO_4$) and evaporated. The residue was subjected to flash chromatography, ethyl acetate - n-hexane (1:1) eluting the title product (459 mg, 80%) which had ir and $^1H$ nmr spectra indistinguishable from those of an authentic sample.

EXAMPLE 2

4,5,6,6a-Tetrahydro-2-(4-methoxyphenyl)-1(3aH)pentalenone

The method of Example 1 was used except that 4-methoxyphenylethyne (740 mg) was dissolved in ethyl acetate and added to $Co_2(CO)_8$ in toluene followed by cyclopentene and $Me_3NO.2H_2O$. After 48 h reaction time the title product (930 mg, 73%) was isolated as a pale yellow oil.

Nmr: δ ($CDCl_3$) 7.69 and 6.91 (4H, AB quartet, $C_6H_4$), 7.58 (1H, d, H-3), 3.82 (3H, s, $OCH_3$), 3.32 (1H, m, H-6a?), 2.89 (1H, m, H-3a?), 1.80 (6H, br m, C$\underline{H}_2$).

EXAMPLE 3

4,5,6,7,8,8a-Hexahydro-2-phenyl-1(3aH)azulenone

The method of Example 1 was repeated using ($PhC_2H$) $Co_2(CO)_6$ (2.30 g, 5.93 mmol), cycloheptene (6.9 ml, 5.7 g, 59 mmol) and $Me_3NO.2H_2O$ (5.27 g, 47.4 mmol) to yield the title product (1.014 g, 75.6%), colourless crystals, m.p. 218° C. (from dichloromethane—light petroleum).

Nmr: δ ($CDCl_3$) 7.71 and 7.35 (ea. 3H, m, H-3, $C_6H_5$), 3.12 (1H, m, H-8a?), 2.70 (1H, m, H-3a?), 1.80 (10H, br m, $CH_2$).

EXAMPLE 4

1,3,6,6a -Tetrahydro-4-pentyl-5H-cyclopentan[c]furan-5-one

"Flash" silica (140 g, 40–60 μm, 400–230 mesh) in a round-bottomed flask was treated with water (14 g) and a solution of (allyl oct-2-ynyl ether)hexacarbonyldicobalt (12.4 g, 27.5 mmol, prepared as described below) in ether was added. The solvent was removed using a rotary evaporator. Air was admitted and the flask was kept rotating on the evaporator while heating to 60° C. for 3 h. The contents were then thoroughly extracted with ether and the extracts evaporated under reduced pressure. Flash chromatography of the residue, eluting with ether—light petroleum (3:1) gave some allyl oct-2-ynyl ether (ca.10%) and the title product as a yellowish oil (2.42 g, 45%). Ir: υmax (film) 1710, 1670, 1460, 1130, 1030, 890 cm$^{-1}$; $^1$H nmr: δ (CDCl$_3$) 4.61 and 4.51 (ea. 1H, d, J=15.5 Hz, H-4), 4.31 (1H, m, H-2), 3.16 (2H, m, H-1 H-2), 2.66 and ca. 2.3 (ea. 1H, m, H-8), 2.38–2.07 (2H, m, =C.CH$_2$CH$_2$), 1.48 (2H, br m, =C.CH$_2$CH$_2$), 1.40–1.18 (4H, m, CH$_2$CH$_2$CH$_3$), 0.88 (3H, t, CH$_3$). $^{13}$C nmr: δ (CDCl$_3$) 208.9 (s, C-7), 175.8 (s, C-5), 137.0 (s, C-6), 71.8 (t, C-4), 64.9 (t, C-2), 43.3 (d, C-1), 38.3 (t, C-8), 31.6 (t, =C.CH$_2$CH$_2$, 27.4, 24.2 and 22.3 (ea. t, CH$_2$CH$_2$CH$_2$CH$_3$), 13.9 (q, CH$_3$).

Allyl oct-2-ynyl ether, CH$_2$=CHCH$_2$OCH$_2$C≡C(CH$_2$)$_4$CH$_3$

Allyl propargyl ether (3.8 g, 40 mmol) in dry THF (20 ml) was cooled to 0° C. and a cooled solution of MeLi.LiBr .(25 ml of a 1.5M solution in ether, 37.5 mmol) was added dropwise. Stirring was continued for 15 min at 0° C. after complete addition, then 1-bromopentane (4.7 ml, 5.7 g, 37.5 mmol) was added dropwise followed, in one portion, by dimethyl sulphoxide (70 ml). The mixture was allowed to warm and stirred at room temperature for 3 h, then cooled to 0° C. before dropwise addition of water. Ether (200 ml) was added to extract the product and after separation, washing the organic layer with brine (½ saturated) and drying (MgSO$_4$) the solution was evaporated under reduced pressure to leave a yellow oil. After filtration through silica gel (10 g), eluting with light petroleum—ether (1:1) the product was distilled at 115° C./40 Torr as a colourless oil (3.4 g, 54%).

Ir: υmax (film) 3090, 2290, 2230, 1460, 1350, 1080, 925cm$^{-1}$. Nmr: δ (CDCl$_3$) 5.93 (1H, m, —CH=), 5.28 (2H, m, CH$_2$=), 4.10 (4H, m, CH$_2$O), 2.22 (2H, m, ≡C—CH$_2$CH$_2$), 1.41 (6H, m, CH$_2$CH$_2$CH$_2$CH$_3$), 0.91 (3H, t, CH$_3$).

(Allyl oct-2-ynyl ether) hexacarbonyldicobalt.

Octacarbonyl-dicobalt (14.0 g, 40.7 mmol) was stirred with light petroleum (100 ml) for 15 min to ensure complete dissolution. Then allyl oct-2-ynyl ether (6.76 g, 40.7 mmol) in the same solvent (25 ml) was added dropwise and the mixture stirred overnight. After filtration through Kieselguhr and concentration, the solution was chromatographed on neutral alumina, eluting with light petroleum. Evaporation of the eluate left the complex (18.0 g, 98%) as a dark red liquid). Ir: υmax (film) 3090, 2090, 2025, 2010, 1860, 1640, 1460, 1340, 1080, 925 cm$^{-1}$.

Nmr: δ (CDCl$_3$) 5.93 (1H, mt —CH=), 5.28 (2H, m, CH$_2$=), 4.65 (2H, s, OCH$_2$C≡), 4.17 (2H, d, OCH$_2$CH=), 2.86 (2H, t, ≡C—CHhd 2CH$_2$), 1.45 (6H, m, CH$_2$CH$_2$CH$_2$CH$_3$), 0.93 (3H, t, CH$_3$). Found: C, 45.3; H, 4.2. C$_{17}$H$_{18}$Co$_2$O$_7$ requires C, 45.2; H, 4.0%.

EXAMPLE 5

4,5,6,6a-Tetrahydro-2-(4-acetylphenyl)-1(3aH) pentalenone

A solution of Perrier complex was prepared from acetyl chloride (663mg, 8.45 mmol) and aluminimum chloride (1.13 g, 8.45 mmol) in dichloromethane (5 ml) and 4,5,6, 6a-tetrahydro-2-phenyl-1(3aH)pentalenone (335 mg, 1.69mmol) in dichloromethane (95 ml) was added at 0° C. The mixture was heated under reflux for 48 h, then poured onto ice, extracted with dichloromethane and the extract washed with aqueous potassium carbonate and dried (MgSO$_4$). After removal of solvent the residue was chromatographed. Ethyl acetate—n-hexane (1:2) eluted unreacted starting ketone (17 mg) followed by the title product (277 mg, 68%), yellowish crystals, m.p. 76–77° C.

Nmr: δ (CDCl$_3$) 7.97 (2H) and 7.81 (3H, AB quartet with overlapping d, C$_6$H$_4$, H-3), 3.40 (1H, m, H-3a?), 2.95 (1H, m, H-6a?), 2.61 (3H, s, CH$_3$), ca 1.80 (6H, br m, CH$_2$).

EXAMPLE 6

Methyl ester of hexahydro-5-oxo-4-pentyl-1H-cyclopentan[c]furan-3a-acetic acid

O-methyl-O-(tert-butyl dimethylsilyl) ketene acetal was prepared according to the method of Kita et al, (1982), J. Chem, Soc. Perkin Trans, 1, 1099 and used as follows:

A solution of 1,3,6,6a-tetrahydro-4-pentyl-5H-cyclopenta [c]furan-5-one (133 mg, 0.68 mmol) in dry dichloromethane (lOml) was cooled to −78° C. and titanium(IV) chloride (157 mg, 0.09 ml, 0.83 mmol) was added, followed, after 5 min, by the ketene acetal (0.46 ml, 383 mg, 2.03 mmol), added in small droplets. After 30 min stirring at 78° C. the mixture was allowed to warm to room temperature and stirring continued overnight. Aqueous potassium carbonate was then added and the product extracted into ethyl acetate. The extracts were dried (MgSO$_4$) and evaporated and the residue subjected to flash chromatography, eluting with ether—light petroleum (3:1). This gave the title product (148 mg, 81%).

Ir: υmax (film 1730,1440, 1365, 1265, 1205, 1180, 1095, 1045, 930 cm$^{-1}$. Found: C, 66.6; H, 9.15. C$_{15}$H$_{24}$O$_4$ requires C 67.1; H, 9.0%. Mass specturm: M/z=268.1680; C$_{15}$H$_{24}$O$_4$ requires 268.1675; base peak: 166.0635; C$_9$H$_{10}$O$_3$ requires 166.0630.

This product was a (nearly 1:1) mixture of two diastereoisomers and the biological test results relate to that mixture. Separation was however effected by further flash chromatography and the following $^1$H nmr data relate to the pure isomers:

Isomer A: δ (CDCl$_3$) 4.17 (1H, dd, J=9.1 Hz, 6.5 Hz, H-4), 3.71, (3H, s, OCH$_3$), 3.55 (3H, m, H-2, H-4), 2.70 (5H, br m, H-5, H-6(1H), H-8, CH$_2$COOMe), 2.05 (1H, dd, J=18.0 Hz, 4.8 Hz, H-6), 1.61 (2H, m, CH$_2$C$_4$H$_9$), 1.28 (6H, m, CH$_2$CH$_2$CH$_2$CH$_3$), 0.89 (3CH$_2$CH$_3$).

Isomer B: δ (CDCl$_3$) 4.09 (1H, m, H-4), 3.80 (1H, d, J=9.1 Hz, H-2), 3.65 (3H, s, OCH$_3$), 3.65 (2H, m, H-2, H-4), 2.68 (2H, m, H-5, H-8), 2.58 (1H, d, J=16.6 Hz, H-9), 2.46 (1H, d, J=16.6 Hz, H-9), 2.23 (2H, m, H-6), 1.60 (2H, m, CH$_2$C$_4$H$_9$), 1.30 (6H, m, CH$_2$CH$_2$CH$_2$CH$_3$), 0.88 (3H, t, CH$_2$CH$_3$).

EXAMPLE 7

Methyl ester of octahydro-2-(4-methoxyphenyl)-3-oxo-1-pentaleneacetic acid

The ketone of Example 2 (828 mg, 3.63 mmol), Me$_3$SiCH=C—(OMe)OSiMe$_3$ (950 mg, 4.35 mmol) and TiCl$_4$ (0.52 ml, 894 mg, 4.71 mmol) in dichloromethane (30 ml) gave the intermediate α-trimethylsilyl ester (1.358 g, crude) which, after reaction with potassium fluoride and flash chromatography gave the title product (405 mg, 37% overall).

Nmr: δ (CDCl$_3$) 6.96 and 6.87 (4H AB quartet, C$_6$H$_4$), 3.79 (3H, s, C$_6$H$_4$OCH$_3$), 3.48 (3H, s, COOCH$_3$), 3.36 (1H, dd, J=13 Hz, 1.5 Hz, H-2), 2.93 (1H, m, H-6a), 2.61 (1H, m, H-3a), 2.49 (2H, dd, J=6.5 Hz, 2.2 Hz, CH$_2$COOMe), 2.20–1.50 (7H, br m, all other H).

EXAMPLE 8

Methyl ester of decahydro-3-oxo-2-phenyl-1-azuleneacetic acid

The ketone of Example 3 (847 mg, 3.74 mmol) and Me$_3$SiCH=C(OMe)OSiMe$_3$ (980 mg, 4.5 mmol) in dichloromethane (10 ml) treated with TiCl$_4$ (0.49 ml, 852 mg, 4.5 mmol) gave the silylated intermediate which was not purified, but treated directly with potassium fluoride (718 mg, 12.35 mmol) in aqueous methanol to give the title keto-ester (1.049 g, 93%)

Nmr: δ (CDCl$_3$) 7.28 (3H) and 7.07 (2H, Ph), 3.41 and 3.39 (together 3H, ea s, OCH$_3$); other peaks are not resolved because this product is undoubtedly a mixture of several stereoisomers.

EXAMPLE 9

Methyl ester of decahydro-3-oxo-2-pentyl-1-azuleneacetic acid

Heptyne (0.52 ml, 379 mg, 3.9 mmol) was added in dichloromethane (40 ml) to octacarbonyldicobalt (1.28 g, 3.75 mmol). After stirring this mixture for 30 min, cycloheptene (4.3 ml, 3.6 g, 37.5 mmol) and acetonitrile (2 ml, 1.54 g, 37.5 mmol) were added and the mixture was refluxed for 5 days. Chromatography on silica, eluting with 30%. chloroform in n-hexane gave a somewhat impure product (586 mg, 71%). Rechromatography followed by distillation at 175° C./1.5 Torr, gave 4,5,6,7,8,8a-hexahydro-2-pentyl-(3aH)azulenone as a colourless oil (378 mg, 46%).

This ketone (345 mg, 1.57 mmol) and Me$_3$SiCH=C(OMe)OSiMe$_3$ 0.47 ml, 0.41 g, 1.88 mmol) in dichloromethane (5 ml) were allowed to react with TiCl$_4$ (0.22 ml, 386 mg, 2.04 mmol) and the resultant product, without isolation treated with KF (300 mg, 5.2 mmol) to give the title keto-ester (336.5 mg, 73%).

Nmr: δ (CDCl$_3$) 3.69 (3H, s, OCH$_3$), 0.87 (3H, t, CH$_2$C$\underline{H}_3$); all other H form poorly resolved multiplets between 2.60 and 1.20 ppm.

EXAMPLE 10

Methyl ester of hexahydro-3-oxo-2-phenylcyclopenta[c]-furan-4-acetic acid 1,3,3a,6a-Tetrahydro-5-phenyl-4H-cyclopenta[c]furan-4-one (2.07 g, 10.3 mmol) and Me$_3$SiCH=C(OMe) SiMe$_3$ (3.43 g, 15.7 mmol) in dichloromethane (50 ml) with TiCl$_4$ (2.03 g, 10.7 mmol) gave the crude a-trimethylsilyl derivative of the title ester (3.76 g) as a yellow oil. Flash chromatography and crystallisation from ether —light petroleum gave two crystalline fractions (presumably diastereisomers), m.p. 71° C. and m.p. 80° C. The lower melting fraction (0.84 g) was stirred overnight with potassium fluoride (0.25 g) in methanol (8 ml) and water (32 ml) to give the title ester (0.60 g, 90%) as a pale yellow oil which solidified on storage and was recrystallised from ethyl acetate—light petroleum, m.p. 60° C.

Found: C, 69.7; H, 6.6. C$_{16}$H$_{18}$O$_4$ requires C, 70.1; H, 6.6%.

EXAMPLE 11

4,5,6,6a-Tetrahydro-2-phenyl-1(3aH)pentalenone
Route 1 Using Me$_3$NO.H$_2$O Hexacarbonyl(phenylacetylene)dicobalt (4.09 g, 10.54 mmol) was placed in a 250 ml flask equipped with a dropping funnel, nitrogen inlet and magnetic stirrer. Toluene (65 ml) and cyclopentene (9.28 ml, 7.18 g, 105 mmol) were added. A solution of trimethylamine-N-oxide dihydrate (9.37 g, 84 mmol) in methanol (20 ml) was then added at a rate of 1 drop per 1–2 min with stirring, which was continued for 3 days. The solution was then concentrated (to remove methanol) and any unreacted trimethylamine-N-oxide extracted with dilute hydrochloric acid. The aqueous extracts were washed with ethyl acetate and the combined organic layers were dried (MgSO$_4$), concentrated and subjected to flash silica chromatography. Hexane/ethyl acetate (10:1) eluted the title ketone (1.682 g, 80%).

Route 2 Using Polar Solvent

To octacarbonyldicobalt (0.873 g, 2.55 mmol) in a 100 ml flask fitted with a reflux condenser and a magnetic stirrer, phenylacetylene (0.29 ml, 2.68 mmol) dissolved in dichloromethane (30 ml) was added and the mixture stirred for 30 min to effect complexation. Cyclopentene (2.24 ml, 25.5 mmol) in methanol (1.03 ml, 25.5 mmol) was then added and the mixture refluxed vigorously for 3 days. The mixture was then filtered through silica, evaporated to dryness, and chromatographed as in the preceding experiment to give unreacted hexacarbonyl (phenylacetylene)dicobalt (104 mg, 10.4%) followed by the title ketone (381.4 mg, 75.4%).

Biological Tests

Using the compounds prepared as described in Examples 1 to 11 above and further compounds of formula II (Examples 12 to 19) prepared as described by Billington et al and Jeong et al referenced above, bioassays were carried out to assess antitranspirant activity and effects on coleoptile growth.

Antitranspirant Activity:

(a) Effects on stomatal aperture were assessed both in vitro and in vivo. For the former, abaxial epidermal strips were removed from glasshouse-grown leaves of the bean, *Vicia faba*, floated on test solution and stomata observed after various time intervals.

(b) For the in vivo study the effect on stomata was assessed indirectly by porometer study of transpiration of growing leaves of *V.faba*.

For the in vitro tests the compounds were used in a concentration range of from 0.1 to 1.0 mM. For the in vivo test a concentration range of 0.1 to 10.0 mM was employed.

Coleoptile Growth:

This test was carried out by assessing the IAA—induced growth of excised segments of barley (*Hordeum sativum*) coleoptiles using a concentration of active compound in the range of 0.1 to 1.0 mM.

The results are given in Table 1 below with the known compounds methyl jasmonate and methyl dihydrojasmonate included for comparison purposes. In the table, blanks relate to tests not yet performed; "–" denotes zero or very weak activity; the number of "+" signs is a measure of the relative activity of the different test substances.

TABLE 1
| Example | Structure | Stomata in vitro | Stomata in vivo | Coleoptile Growth |
|---|---|---|---|---|
| 1 | 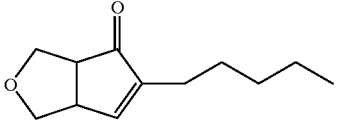 | ++++ | ++ | ++ |
| 2 | 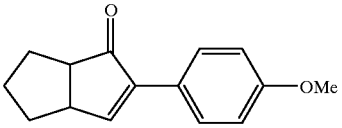 | +++ | ++++ | ++ |
| 3 | 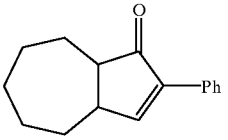 | ++++ | ++ | + |
| 4 | 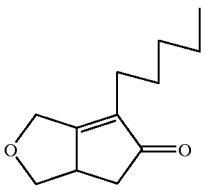 | ++++ | − | − |
| 5 | 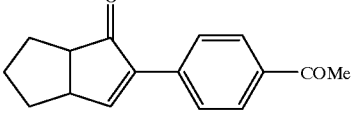 | ++ | ++ | ++ |
| 6 | 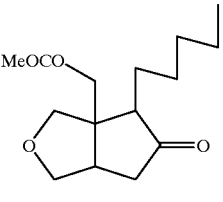 | ++++ | ++++ | ++++ |
| 7 | 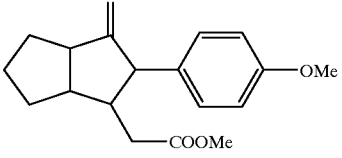 | ++++ | ++++ | ++++ |
| 8 | 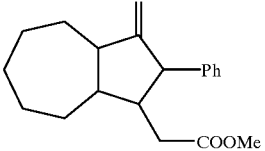 | ++ | + | ++ |

TABLE 1-continued

| Example | Structure | Stomata in vitro | Stomata in vivo | Coleoptile Growth |
|---------|-----------|------------------|-----------------|-------------------|
| 9 | (bicyclic ketone with pentyl and CH2COOMe substituents) | ++ | ++++ | ++++ |
| 10 | (oxa-bicyclic ketone with Ph and CH2COOMe) | +/− | − | +++ |
| 11 | (bicyclic enone with Ph) | ++ | +++ | ++++ |
| 12 | (dimethyl oxa-bicyclic enone) | ++ | − | + |
| 13 | (methyl oxa-bicyclic enone) | ++++ | − | − |
| 14 | (oxa-bicyclic enone with Ph) | + | ++++ | − |
| 15 | (bicyclic enone with pentyl) | ++++ | − | +++ |
| 16 | (tricyclic enone with pentyl) | ++++ | ++ | ++++ |
| 17 | (bicyclic ketone with Ph and CH2COOMe) | ++ | +++ | + |

TABLE 1-continued

| Example | Structure | Stomata in vitro | Stomata in vivo | Coleoptile Growth |
|---|---|---|---|---|
| 18 | 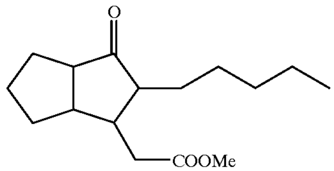 | ++++ | +++ | ++++ |
| 19 | 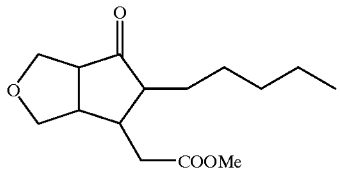 | + | ++ | +++ |
| methyl jasmonate (comparison) | 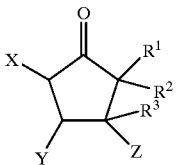 | ++ | ++ | ++++ |
| methyl dihydro-jasmonate (comparison) | 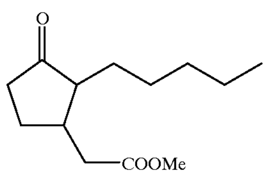 | +++ | + | ++ |

What is claimed is:

1. A method of inhibiting plant growth of a compound formula II in which either the pair of symbols X and Y or the pair of symbols Y and Z, together with the carbon atoms to which they are attached, form a non-aromatic ring system having either 5 or 7 ring atoms, all of which are carbon except that one may be oxygen, and which is substituted or unsubstituted, $R^1$ represents a hydrogen atom or an alkyl or a substituted or unsubstituted phenyl group and either $R^2$ represents a hydrogen atom and $R^3$ an alkyl carboxymethyl group, in which case the ring shown in formula II is a cyclopentanone ring, or $R^2$ and $R^3$ together form a double bond, thus forming a cyclopentenone ring, and thereafter any unsatisfied valencies of ring carbon atoms of the cyclopentanone or cyclopentenone ring are satisfied by hydrogen atoms.

2. A method according to claim 1 wherein said inhibition is effected at least partially by controlling transpiration or shoot growth.

3. A method according to claim 1 wherein X and Y or Y and Z, together with the carbon atoms to which they are attached, form a cyclopentane, cycloheptane, [2.2.0] bicyclohexene or a tetrahydrofuran ring.

4. A method according to claim 3 wherein the tetrahydrofuran ring is fused at the 3 and 4 positions to the cyclopentanone or cyclopentenone ring.

5. A method according to claim 1 wherein $R^1$ represents an alkyl group of 1 to 6 carbon atoms or a phenyl, p-alkoxyphenyl or p-alkylcarbonyl phenyl group in which the alkoxy and alkyl groups have 1 to 4 carbon atoms.

6. A method according to claim 5 wherein $R^1$ is p-methoxy- or p-acetyl-substituted phenyl or n-pentyl.

7. A method according to claim 1 wherein $R^3$ represents an alkyl carboxymethyl group in which the alkyl group has from 1 to 4 carbon atoms.

8. A composition useful for inhibiting plant growth, which comprises a compound of formula II defined in claim 1, together with an agriculturally or horticulturally acceptable carrier, said carrier comprising a dispersible inert finely divided carrier solid or a carrier liquid which includes a surface active agent.

9. A composition according to claim 8, wherein $R^1$ represents an alkyl group of 1 to 6 carbon atoms or a phenyl, p-alkoxyphenyl or p-alkylcarbonyl phenyl group in which the alkoxy and alkyl groups have 1 to 4 carbon atoms.

10. A composition according to claim 9 wherein $R^1$ is p-methoxy- or p-acetyl-substituted phenyl or n-pentyl.

11. A composition according to claim 8 wherein $R^3$ represents an alkyl carboxymethyl group in which the alkyl group has from 1 to 4 carbon atoms.

* * * * *